United States Patent [19]

Hoshowski et al.

[11] Patent Number: 5,254,336
[45] Date of Patent: Oct. 19, 1993

[54] METHOD OF INCREASING HAIR SHINE AND REPAIRING ALKALINE-DAMAGED HAIR

[75] Inventors: Myra A. Hoshowski, Addison; Chaitanya Patel, Glen Ellyn, both of Ill.

[73] Assignee: Helene Curtis, Inc., Chicago, Ill.

[21] Appl. No.: 950,817

[22] Filed: Sep. 24, 1992

[51] Int. Cl.$^5$ .......................... A61K 7/06; A61K 7/08
[52] U.S. Cl. ...................................... 424/70; 8/127.51; 132/202; 132/204; 132/205; 252/142; 252/DIG. 13; 424/71; 424/401
[58] Field of Search .............................. 424/70, 71, 401; 252/142, DIG. 13; 132/202, 204, 205; 8/127.51

[56] References Cited

U.S. PATENT DOCUMENTS

| | | | |
|---|---|---|---|
| 3,910,289 | 10/1975 | Wajaroff et al. | 132/205 |
| 3,996,146 | 12/1976 | Tarasov et al. | 252/DIG. 13 X |
| 4,134,411 | 1/1979 | Yamazaki | 132/205 |
| 4,275,748 | 6/1981 | Graziano | 132/202 |
| 4,828,750 | 5/1989 | Simion et al. | 252/142 |
| 5,148,822 | 9/1992 | Akhtar | 132/204 |

FOREIGN PATENT DOCUMENTS 401454A 12/1990 European Pat. Off. .
89/00648 12/1989 Fed. Rep. of Germany .
2-68303 12/1991 Japan .

*Primary Examiner*—Thurman K. Page
*Assistant Examiner*—Robert H. Harrison
*Attorney, Agent, or Firm*—Marshall, O'Toole, Gerstein, Murray & Borun

[57] ABSTRACT

A method of treating hair that has been damaged and/or dulled as a result of an alkaline hair treatment including contacting the hair with a solution of weak acid having a pH in the range of about 2.0 to about 5.0, preferably about 2.0 to about 3.8 and having at least 0.75 milliequivalent of free acid per milliliter of solution, to restore natural shine to the dulled hair and to repair uplifted cuticles, if any, that have resulted from the alkaline hair treatment.

19 Claims, No Drawings

METHOD OF INCREASING HAIR SHINE AND REPAIRING ALKALINE-DAMAGED HAIR

FIELD OF THE INVENTION

The present invention is directed to a method of treating hair that has been chemically damaged and/or left in a dull, non-shiny condition as a result of contact with an alkaline hair treating composition, such as an alkaline permanent wave treatment, or a soap film on the hair, to repair the hair damage and/or increase hair shine. More particularly, the present invention is directed to a solution containing a weak acid in an amount of about 0.05% to about 1.0% by weight containing at least 0.75 milliequivalent of free acid per milliliter of solution, capable of repairing uplifted hair cuticles resulting from alkaline treatment and capable of restoring natural shine to hair that has been dulled as a result of alkaline hair treatment compositions, such as alkaline permanent waves.

BACKGROUND OF THE INVENTION AND PRIOR ART

Recently, body soaps, in bar form, have been developed to provide dual purposes of a body soap and a shampoo for the hair. Such body soap/shampoo compositions can include hair conditioners for softness and manageability of the hair and include a natural soap base or a combination of a natural soap base, e.g., a metal salt of a fatty acid, such as a sodium or potassium salt, with a synthetic detergent soap base so that the composition can cleanse the body as well as the hair while leaving the hair soft and manageable.

One example of such a product is disclosed in the Tibbetts, et al. U.S. Pat. No. 4,919,838. While such products are adequate for cleansing both the body and the hair, even when such products contain hair conditioners, such bar soaps are significantly alkaline, thereby damaging the hair cuticle at times, and leave a film of soap on the hair shaft that significantly dulls the natural hair shine.

Other alkaline hair-treating compositions that can cause significant damage to hair and leave the hair in a dull, non-shiny condition include alkaline permanent wave compositions, such as those disclosed in this assignee's Kolc, et al. U.S. Pat. No. 4,913,900; as well as tinting, frosting, and bleaching compositions; environmental conditions, such as climate and pollution; antidandruff shampoo compositions, and other treatments that leave a solid residue on the hair shaft.

The reducing agent step of a permanent wave process and, in particular, alkaline thioglycolates, can cause significant damage to the hair cuticle since alkaline salts of thioglycolic acid, e.g., the ammonium salt of thioglycolic acid (pKa=10.4) have acceptable waving efficiency only if the pH of solution exceeds 9. If the pH of the reducing agent composition is in the range of about 10 to about 12, the hair cuticle can be uplifted at a number of sites on the hair cuticle and the hair can be significantly dulled and remain dull even after oxidation to complete the permanent waving process.

A Japanese patent application, HEI 2-68303 discloses a composition that is capable of eliminating odor resulting from treating hair with a cysteamine hair processing agent. This composition has a pH of about 2.0–2.7 and contains 0.1–0.5 milliequivalent of free acid per milliliter. If the pH of this composition is above 2.7, removal of odor is insufficient; and if the amount of acid per milliliter is above 0.5 milliequivalent, the hair is hardened and damaged.

A published European patent application 0 401 454 teaches the use of at least 5% ascorbic acid for prevention of oxidative damage to the hair by hydrogen peroxide.

In accordance with the present invention, it has been found that a solution of weak acid having a pH in the range of about 2.0 to about 5.5, particularly having a pH of about 2.0 to about 4.0, and having at least 0.75 milliequivalent of free acid per milliliter of solution, repairs hair that has been damaged by an alkaline treatment, such as the reducing agent lotion step of the permanent waving process, while restoring full shine to dulled hair that has been dulled as a result of an alkaline treatment of, or retention of solid residue on the hair.

SUMMARY OF THE INVENTION

In brief, the present invention is directed to a method of treating hair that has been damaged and/or dulled as a result of an alkaline hair treatment including contacting the hair with a solution of weak acid having a pH in the range of about 2.0 to about 5.0, preferably about 2.0 to about 3.8 and having at least 0.75 milliequivalent of free acid per milliliter of solution, to restore natural shine to the dulled hair and to repair uplifted cuticles, if any, that have resulted from the alkaline hair treatment.

Accordingly, one aspect of the present invention is to provide a new and improved method of post-alkaline hair treatment capable of substantially increasing the hair shine and/or repairing uplifted cuticles resulting from harsh alkaline hair treatment.

Another aspect of the present invention is to provide a method of treating alkaline permed hair with a weak acid solution having a pH of about 2.0 to about 3.8 and containing at least 0.75 milliequivalent of free acid per milliliter of solution to fully restore hair shine to alkaline-dulled hair.

The above and other aspects and advantages of the present invention will become more apparent from the following detailed description of the preferred embodiments.

DETAILED DESCRIPTION OF THE PREFERRED EMBODIMENTS

Hair that is treated with alkaline compositions may be damaged and can appear dull. Recently, combination soap/shampoo products have been introduced and with the natural movement, consumers have been using bar soap to wash their hair. This creates a need for products which can effectively remove the resulting dull film. Also, treatment with alkaline materials, such a permanent waves, hair color, and the like damages the hair, leaving it dull.

Surprisingly, it has been found that only small amounts of a weak acid, having a pKa in the range of about 4.0 to about 7.0, is needed to restore shine to the hair. Even more surprisingly, it has been found that the damage caused by an alkaline permanent wave is eliminated by the method of the present invention.

The weak acids that are useful in the acid solutions, used in the method of the present invention include:

| Acid and Concentration | pH of Solution |
| --- | --- |
| Tartaric, 0.1N | 2.2 |
| Malic, 0.1N | 2.2 |
| Citric, 0.1N | 2.2 |

-continued

| Acid and Concentration | pH of Solution |
|---|---|
| Formic, 0.1N | 2.3 |
| Lactic, 0.1N | 2.4 |
| Acetic, N | 2.4 |
| Acetic, 0.1 N | 2.9 |
| Acetic, 0.01N | 3.4 |
| Benzoic, 0.01N | 3.1 |
| Alum, 0.1N | 3.2 |
| Carbonic (saturated) | 3.8 |
| Hydrogen sulfide, 0.1N | 4.1 |
| Arsenious (saturated) | 5.0 |

The acid solution, in order to be effective to completely restore shine to alkaline-dulled hair, should have a pH in the range of about 2.0 to about 5.0. To achieve the full advantage of the present invention, the pH of the acid-treating solution should be in the range of about 2.0 to about 3.8 in order to completely restore alkaline-dulled hair to its natural shine. Further, the acid solution should contain at least 0.75 milliequivalent of free acid per milliliter of solution and up to about 2.0 milliequivalent of acid per milliliter of solution. If the pH of the acid-treating solution is below about 2.0, hair damage may result. If the pH of the acid-treating solution is above about 5.0, very little shine improvement is experienced.

Surprisingly, it has been found that a weak solution of citric acid provides noticeably more shine restoration to alkaline-dulled hair than other weak acids. Accordingly, it is preferred that the acid-treating solution of the present invention used in the method of the present invention is citric acid. It has been found that an acid-treating solution containing about 0.05% citric acid to about 1% by weight citric acid, preferably about 0.1% to about 0.5% citric acid, significantly improves the shine on alkaline-treated dulled hair and, more surprisingly, restores uplifted cuticles resulting from harsh alkaline hair treatments, such as alkaline permanent wave reducing compositions.

Examples of suitable acid-treating solutions useful in the method of the present invention are as follows:

EXAMPLE 1

| Composition: Item # | Description | Wt. % |
|---|---|---|
| 1 | SOFT WATER | 99.56960 |
| 2 | CITRIC ACID (50% active in H₂O) | 0.25000 |
| 3 | PEG-15 NONYL PHENYL ETHER (fragrance solubilizer) | 0.02000 |
| 4 | FRAGRANCE | 0.01000 |
| 5 | DMDM HYDANTOIN (Preservative) | 0.10000 |
| 6 | METHYLCHLOROISOTHIAZOLINONE/METHYLISOTHI-APOLINONE (Preservative) | 0.05000 |
| 7 | ASCORBIC ACID | 0.00010 |
| 8 | LACTIC ACID, 88% | 0.00010 |
| 9 | D & C RED #33 (100%) | 0.00005 |
| 10 | FD & C BLUE #1 | 0.00015 |

Manufacturing Steps

1. ADD THE CITRIC, LACTIC AND ASCORBIC ACIDS TO THE WATER.
2. PRE-MIX THE PEG-15 NONYL PHENYL ETHER AND THE FRAGRANCE, ADD TO THE BATCH. MIX UNTIL UNIFORM.
3. ADD THE PRESERVATIVES.
4. ADD THE COLORS.

EXAMPLE 2

| Composition: Item # | Description | Wt % |
|---|---|---|
| 1 | SOFT WATER | 99.50000 |
| 2 | CITRIC ACID (50% active in H₂O) | 0.50000 |

EXAMPLE 3

| Composition: Item # | Description | Wt % |
|---|---|---|
| 1 | SOFT WATER | 98.97000 |
| 2 | CITRIC ACID (50% active in H₂O) | 1.00000 |
| 3 | PEG-15 NONYL PHENYL ETHER (fragrance solubilizer) | 0.02000 |
| 4 | FRAGRANCE | 0.01000 |

Manufacturing Steps

1. ADD THE CITRIC TO THE WATER.
2. PRE-MIX THE PEG-15 NONYL PHENYL ETHER AND THE FRAGRANCE, ADD TO THE BATCH. MIX UNTIL UNIFORM.

EXAMPLE 4

| Composition: Item # | Description | Wt % |
|---|---|---|
| 1 | SOFT WATER | 99.01980 |
| 2 | CITRIC ACID (50% active in H₂O) | 0.80000 |
| 3 | PEG-15 NONYL PHENYL ETHER (fragrance solubilizer) | 0.02000 |
| 4 | FRAGRANCE | 0.01000 |
| 5 | DMDM HYDANTOIN (Preservative) | 0.10000 |
| 6 | METHYLCHLOROISOTHIAZOLINONE/METHYLISOTHIAZOLINONE (Preservative) | 0.05000 |

| Composition: Item # | Description | Wt % |
|---|---|---|
| 7 | D & C RED #33 (100%) | 0.00005 |
| 8 | FD & C BLUE #1 | 0.00015 |

Manufacturing Steps

1. ADD THE CITRIC, LACTIC AND ASCORBIC ACIDS TO THE WATER.
2. PRE-MIX THE PEG-15 NONYL PHENYL ETHER AND THE FRAGRANCE, ADD TO THE BATCH. MIX UNTIL UNIFORM.
3. ADD THE PRESERVATIVES.
4. ADD THE COLORS.

The compositions also can include anionic, cationic, amphoteric or nonionic surfactants in an amount of about 0.1% to about 20% by weight to impart cleansing and/or emulsifying properties to the composition. Likewise, the compositions can contain other emulsifiers, humectants and similar materials to provide conditioning properties, aesthetic properties and desirable physical properties to the hair.

For example, representative nonionic surfactants include esters of polyols and sugars; the polyethoxylated and/or polypropoxylated alkylphenols; the polyhydroxylated polyethers of fatty alcohols; and the condensation products of ethylene oxide with long chain mercaptans or long chain amides. Similarly, representative anionic surfactants include alkali metal salts, ammonium salts or salts of amines or amino alcohols of fatty acids such as oleic acid; of the sulfates of fatty alcohols, principally $C_{12}$-$C_{14}$ and $C_{16}$ fatty alcohols; of the sulfates of polyethoxylated fatty alcohols; the alkylbenzenesulfonates, such as those wherein the alkyl moiety has 12 carbon atoms; or the alkylarylpolyether sulfates and monoglyceride sulfates. All these nonionic and anionic surfactants, as well as numerous others not cited here, are well known in the art and are fully described in the literature.

More particularly, typical cleansing surfactants include anionic surfactants such as the magnesium, sodium, ammonium, potassium or triethanolamine salts of lauryl sulfate and lauryl ether sulfate; nonionic surfactants such as fatty acid alkanolamides, like lauric acid diethanolamide (lauramide DEA), lauramide MEA (monoethanolamide), cocamide DEA, cocamide MEA, capramide DEA, ricinoleamide DEA, soyamide DEA, myristamide DEA, stearamide DEA, oleylamide DEA, tallowamide DEA, lauramide MIPA, stearamide MEA, tallowamide MEA, isostearamide MEA, isostearamide DEA, myristamide MEA or combinations thereof; and amphoteric surfactants such as N-cocamidopropyl dimethyl glycine. The anionic surfactants, such as the sodium, magnesium, ammonium, potassium and triethanolamide salts of lauryl sulfate, are preferred because they provide richer and more stable foam than other cleansing surfactants at comparable concentrations. All these nonionic, amphoteric and anionic surfactants, as well as numerous others not cited herein, are well known in the art and are fully described in the literature. Many additional anionic, cationic, nonionic and amphoteric surfactants are described in McCUTCHEON'S DETERGENTS AND EMULSIFIERS, 1989 ANNUAL, published by McCutcheon Division, MC Publishing Co., and herein incorporated by reference.

In order to show the surprising hair shine restoration ability of the method of the present invention, hair was first dulled with a bar soap solution and then treated with the citric acid solution of Example 1 at varying concentrations of citric acid to show the significant shine improvement as well as the importance of the pH of the treating solution, as follows. In order to dull the hair, chips of Ivory soap were added to water to make a 10% solution, by weight. The solution was heated until all soap chips were dissolved and a uniform solution was obtained. The solution was then stirred until cool forming a soap solution having a pH of 10.053. Four brown hair tresses weighing 4 grams each were washed with 2 grams each of the soap solution and each was allowed to air dry overnight at room temperature. All tresses washed with soap solution appeared dull. Citric acid was added to water to prepare rinse solutions having the following pH values: 5.465, 4.422, 3.802 and 3.513. Also, a 0.5 milliequivalent solution of citric acid (0.00327%), pH=6.265, was prepared for comparison.

Ten milliliters of each of the above acid solutions were applied to the dull tresses. The solutions were allowed to remain on the hair for two minutes and then rinsed with 100° F. Chicago tap water for 30 seconds. The tresses were then allowed to air dry overnight. Shine was evaluated visually using the following scale: 1=dull; 3=shiny. The results were as follows:

| pH of rinse | Shine value |
|---|---|
| no rinse (soap only) | 1 dull |
| (0.5 me) 6.265 | 1 dull |
| 5.465 | 2.50 slight dulling |
| 4.422 | 2.75 slight dulling |
| 3.802 | 3 shiny |
| 3.513 | 3 shiny |
| 2.0 | 3 shiny |
| no soap | 3 shiny |

Further, the capability of the method of the present invention to smooth uplifted cuticles in hair damaged by alkaline treatments was evaluated as follows. Hair was first damaged with an alkaline waving lotion and compared before and after treatment with the acid solution of Example 1 as follows: two bundles of six hair fibers, made from a pre-washed tress, were used for this experiment. Each bundle was treated with an alkaline waving lotion (Impact Perm) and rinsed. The samples were not neutralized. One bundle was then treated with the acid solution of Example 1 while the other was left as an untreated control.

After air drying, the fibers were affixed to sample stubs containing double-sided adhesive tape. The samples were examined by scanning electron microscopy (SEM) at various magnifications.

The fibers in the untreated control sample were found to contain uplifted cuticles while those in the bundle treated with treating solution of Example 1 did not. Photomicrographs of representative fibers were attached.

Optionally, the acid-treating composition used in the method of the present invention may include a conditioner to improve the combing and manageability of the hair. Particularly, suitable conditioners are the polymeric quaternary ammonium salts, such as Polyquaternium 1 through Polyquaternium 14, inclusive, conditioners defined on page 245, CTFR Cosmetic Ingredient Dictionary, Third Edition, 1982, hereby incorporated by reference. The preferred conditioners are Polyquaternium-4, Polyquaternium-10 and Polyquaternium-11. The conditioner, when added, is included in an amount of about 0.0–1% to about 2.0% by weight of the composition.

Other common cosmetic additives can be incorporated into the acid-treating composition of the method of the present invention, as long as the basic property of hair shine restoration is not substantially adversely affected. These additives include, but are not limited to, commonly used fragrances, dyes, opacifiers, pearlescing agents, thickeners, foam stabilizers, preservatives, water softening agents, acids, bases, buffers and the like; and will usually be present in weight percentages of less than about 1% each, and about 2% to about 5% in total. The composition vehicle is predominantly water but organic solvents also can be added to the composition in order to solubilize optional additive compounds that are not sufficiently soluble in water. Suitable solvents include the lower alcohols, such as ethanol and isopropanol and mixtures.

The acid-treating composition used in the method of the present invention optionally can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners, such as bentonite. These thickeners, when included, preferably are present in an amount from about 0.1% to about 10% by weight and, in particular, from about 0.5% to about 3% by weight, based on the total weight of the composition.

The composition has the pH in the range of about 2.0 to about 5.0, preferably, about 2.0 to about 3.8. To achieve the full advantage of the present invention, the composition has a pH of about 2.0 to about 3.5 and contains about 1 milliequivalent of free acid per milliliter.

What is claimed is:

1. A method of restoring shine to hair that has been dulled as a result of contact with an alkaline hair treating composition comprising:
   contacting the hair with an acid solution consisting essentially of acid and water having an acid concentration of 0.05% to 1.0% by weight, having a pH in the range of about 2.0 to about 3.8 and containing at least about 0.75 milliequivalent of free acid per milliliter of acid solution; and
   rinsing the hair with water.

2. The method of claim 1, wherein the acid has a pKa in the range of about 4 to 7.

3. The method of claim 2, wherein the acid is an acid selected from the group consisting of tartaric, malic, citric, formic, lactic, acetic, benzoic, alum, carbonic, and mixtures thereof.

4. The method of claim 1, wherein the acid is citric acid.

5. The method of claim 1, wherein the acid solution has an acid concentration in the range of about 0.05% to about 0.5% by weight.

6. The method of claim 1, wherein the acid solution is an aqueous solution of citric acid, ascorbic acid and lactic acid.

7. A method of repairing damaged hair that includes uplifted cuticles resulting from contact with an alkaline hair treating composition comprising:
   contacting the hair with an acid solution consisting essentially of acid and water having an acid concentration of about 0.05T to about 1.0% by weight, having a pH in the range of about 2.0 to about 3.8 and containing at least about 0.75 milliequivalent of free acid per milliliter of acid solution; and
   rinsing the hair with water.

8. The method of claim 7, wherein the acid has a pKa in the range of about 4 to about 7.

9. The method of claim 8, wherein the acid is an acid selected from the group consisting of tartaric, malic, citric, formic, lactic, acetic, benzoic, alum, carbonic, and mixtures thereof.

10. The method of claim 7, wherein the acid is citric acid.

11. The method of claim 7, wherein the acid solution has an acid concentration in the range of about 0.05% to about 0.5% by weight.

12. The method of claim 7, wherein the acid solution is an aqueous solution of citric acid, ascorbic acid and lactic acid.

13. A method of cleansing hair and increasing shine on the cleansed hair comprising contacting the hair with a solid alkaline soap containing a metal salt of a fatty acid to cleanse the hair and to dull the hair;
   thereafter contacting the hair with an acid solution consisting essentially of acid and water having an acid concentration in the range of about 0.05% to about 1.0% by weight, having a pH in the range of about 2.0 to about 3.8, and containing at least about 0.75 milliequivalent of free acid per milliliter of acid solution; and rinsing the hair with water.

14. The method of claim 13, wherein the acid has a pKa in the range of about 4 to about 7.

15. The method of claim 14, wherein the acid is an acid selected from the group consisting of tartaric, malic, citric, formic, lactic, acetic, benzoic, alum, carbonic, and mixtures thereof.

16. The method of claim 13, wherein the acid is citric acid.

17. The method of claim 13, wherein the acid solution has an acid concentration in the range of about 0.05% to about 0.5% by weight.

18. The method of claim 13, wherein the acid solution is an aqueous solution of citric acid, ascorbic acid and lactic acid.

19. A method of restoring shine to hair that has been dulled as a result of contact with an alkaline hair treating composition comprising:
   contacting the hair with an aqueous solution consisting essentially of water and an acid having an acid concentration of 0.05% to about 1.0% by weight, having a pH in the range of about 2.0 to about 3.8 and containing at least about 0.75 milliequivalent of free acid per milliliter of solution and an additive selected from the group consisting of fragrances, dyes, opacifiers, pearlescing agents, thickeners, foam stabilizers, preservatives, water softening agents, bases, buffers, conditioning agents and mixtures thereof, in an amount in the range of 0–5% by weight; and
   rinsing the hair with water.

* * * * *

UNITED STATES PATENT AND TRADEMARK OFFICE
CERTIFICATE OF CORRECTION

PATENT NO.  : 5,254,336
DATED       : OCTOBER 19, 1993
INVENTORS   : MYRA A. HOSHOWSKI and CHAITANYA PATEL It is certified that error appears in the above-identified patent and that said Letters Patent is hereby corrected as shown below:

Column 3, line 50, after "about" delete "l%" and substitute therefor -- 1% --;

Column 4, line 52, after "CITRIC" insert -- ACID --;

Column 5, lines 9-10, after "CITRIC" delete ", LACTIC AND ASCORBIC ACIDS" and substitute therefor -- ACID --;

Column 7, line 10, after "about" delete "0.0-1%" and substitute therefor -- 0.01% --;

Column 8, line 9, after "0.05" delete "T" and substitute therefor -- % --;

Signed and Sealed this

Nineteenth Day of July, 1994

Attest:

BRUCE LEHMAN

Attesting Officer     Commissioner of Patents and Trademarks